United States Patent [19]
Warawa et al.

[11] Patent Number: 5,807,897
[45] Date of Patent: Sep. 15, 1998

[54] AMINOTETRALIN DERIVATIVE AND COMPOSITIONS AND METHOD OF USE THEREOF

[75] Inventors: Edward John Warawa, Wilmington, Del.; Bernard Migler, Cherry Hill, N.J.

[73] Assignee: Zeneca Limited, London, United Kingdom

[21] Appl. No.: 804,195

[22] Filed: Feb. 21, 1997

Related U.S. Application Data

[60] Provisional application No. 60/012,640 Mar. 1, 1996.
[51] Int. Cl. $^6$ ...................... A61K 31/135; C07C 217/74
[52] U.S. Cl. ............................................ 514/657; 564/428
[58] Field of Search .............................. 564/428; 514/657

[56] References Cited

U.S. PATENT DOCUMENTS

| | | | |
|---|---|---|---|
| 4,320,148 | 3/1982 | DeMarinis | 564/428 |
| 5,225,596 | 7/1993 | Carlsson et al. | 564/428 |
| 5,376,687 | 12/1994 | Hacksell et al. | 514/657 |

FOREIGN PATENT DOCUMENTS

| | | |
|---|---|---|
| 450238-A | 10/1991 | European Pat. Off. |
| 451022-A | 10/1991 | European Pat. Off. |

OTHER PUBLICATIONS

Rusterholz et al., Arch. Int. Pharmacodyn. 1978, 232, 246–260.
Barfknecht et al., J. Med Chem. 1973, 16(7), 804–808.
Rusterholz et al. J. Med Chem. 1976, 19(1), 99–102.
DeMarinis et al., J. Med. Chem. 1982, 25, 136–141.
Demarinis et al., J. Med. Chem. 1983, 26, 1215–1218.
Arvidsson et al., J. Med. Chem. 1981, 24, 921–923.
Karlsson et al., Acta Chemica Scandinavica, 1988, B42, 231–236.
Bjork et al., J. Med. Chem. 1989, 32, 779–783.
Troanska et al., Arch. Pharm. (Weinheim) 1987 320, 625–629.
Nozulak et al., J. Med. Chem. 1992, 35, 480–489.
Sharabi et al., Research Communication in Chemical Pathology and Pharmacology 1978, 19(1), 37–55.
Cheng et al., Arch. Int. Pharmacodyn. 1974, 208, 264–273.
Arneric et al., Arch. Int. Pharmacodyn. 1982, 258, 84–99.
Arneric et al., Arch. Int. Pharmacodyn. 1982, 257, 263–273.
DeMarinis et al., J. Med. Chem. 1981, 24(12), 1432–1437.
Hieble et al., Naunyn–Schmiedeberg's Arch. Pharmacol. 1982, 318.267–273.
Holz et al., Psychopharmacology 1982, 77, 259–267.
Jim et al., European Journal of Pharmacology 1985, 107, 199–208.
Rusterholz et al., European Journal of Phamacology 1980, 65, 201–211.
Delgado et al., Eur. J. Med. Chem. 1988, 23, 31–38.
Perez et al., IL Farmaco 1991, 46(10), 1155–1166.
Singh et al., Indian Journal of Chemistry 1983, 22B,1076–1078.
Delgado et al., Anales de Qimica 1987, 83, 322–327.
Bhatnagar et al., Pharmacology Biochemistry & Behavior 1982, 17(1), 11–19.
Arvidsson et al., J. Med Chem. 1984, 27, 45–51.
Ames et al., J. Chem. Soc. 1965, 2636–2641.

*Primary Examiner*—Richard L. Raymond
*Attorney, Agent, or Firm*—Paul R. Darkes

[57] ABSTRACT

The invention relates to aminotetralin derivatives of the formula I:

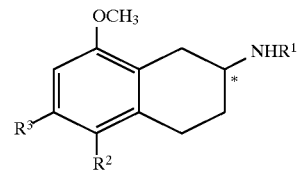

wherein:

$R^1$ is methyl or ethyl; $R^2$ is hydrogen, halogen, lower-alkoxy or thiolower-alkyl; $R^3$ is hydrogen, halogen, lower-alkoxy or lower-alkyl; and the chiral center * is in the (S)(–) form; or a pharmaceutically acceptable acid-addition salt thereof, with the proviso that when $R^2$ and $R^3$ are both hydrogen, $R^1$ must be methyl; to pharmaceutical compositions containing them and to methods for the treatment or prevention of movement disorders utilizing them.

16 Claims, No Drawings

AMINOTETRALIN DERIVATIVE AND COMPOSITIONS AND METHOD OF USE THEREOF

This application claims the benefit of U.S. Provisional Application Ser. No. 60/012,640, filed on Mar. 1, 1966.

The invention relates to aminotetralin derivatives, to pharmaceutical compositions containing the same and to the method of use thereof in the treatment or prevention of movement disorders.

More specifically, the invention relates to compounds of the Formula I:

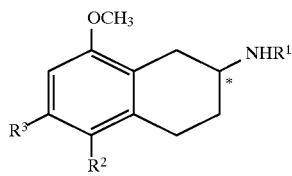

wherein:

$R^1$ is methyl or ethyl; $R^2$ is hydrogen, halogen, lower-alkoxy or thiolower-alkyl; $R^3$ is hydrogen, halogen, lower-alkoxy or lower-alkyl; and the chiral center * is in the (S)(−) form; or a pharmaceutically acceptable acid-addition salt thereof, with the proviso that when $R^2$ and $R^3$ are both hydrogen, $R^1$ must be methyl.

The compounds of the Formula I have been found to suppress involuntary movements and thus are useful in the treatment or prevention of movement disorders, preferably tardive dyskinesia.

Preferred compounds of the Formula I above are those wherein $R^1$ is methyl or ethyl; $R^2$ is hydrogen, bromo, methoxy, ethoxy or thiomethyl; and $R^3$ is hydrogen or halogen.

Particularly preferred compounds of the Formula I above are those wherein $R^1$ is methyl or ethyl; $R^2$ is hydrogen, bromo, methoxy, ethoxy or thiomethyl, and $R^3$ is hydrogen.

Preferred species of the invention are (−)-N-methyl-(2S)-2-amino-5,8-dimethoxytetralin hydrochloride and (−)-N-methyl- (2S) -2-amino-8-methoxytetralin.

Another preferred species of the invention is (−)-N-methyl- (2S) -2-amino-8-methoxytetralin hydrochloride.

The invention further relates to pharmaceutical compositions which comprise a compound of the Formula I together with a pharmaceutically acceptable carrier, adjuvant, diluent or vehicle.

The invention further relates to a method for the treatment or prevention of movement disorders which comprises administering to a patient in need of such treatment an effective amount of a compound of the Formula I:

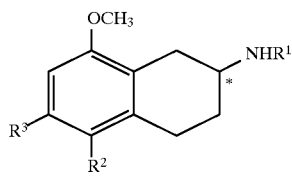

wherein:

$R^1$ is methyl or ethyl; $R^2$ is hydrogen, halogen, lower-alkoxy, or thiolower-alkyl; $R^3$ is hydrogen, halogen, lower-alkoxy or lower-alkyl; and the chiral center * is in the (S)(−) form or the (R,S) form; or a pharmaceutically acceptable acid-addition salt thereof; with the provisos that (a) when $R^2$ and $R^3$ are both hydrogen, $R^1$ must be methyl and (b) when the chiral center * is in the (R,S) form the proportion of the (S)(−) form must be 50% or greater.

Preferred compounds of the Formula I for use in the method described above are those wherein $R^1$, $R^2$ and $R^3$ are as defined directly above and the chiral center * is in the (S)(−) form.

Particularly preferred compounds of the Formula I for use in the method described above are those wherein $R^1$ is methyl or ethyl; $R^2$ is hydrogen, bromo, methoxy, ethoxy, or thiomethyl; and $R^3$ is hydrogen or halogen.

Especially particularly preferred compounds of the Formula I for use in the method described above are those wherein $R^1$ is methyl or ethyl; $R^2$ is hydrogen, bromo, methoxy, ethoxy, or thiomethyl; and $R^3$ is hydrogen.

Preferred species of the Formula I for use in the method described above are those selected from the group consisting of:

N-methyl-2-amino-5,8-dimethoxytetralin hydrochloride;

(−)-N-methyl-(2S)-2-amino-5,8-dimethoxytetralin hydrochloride;

N-ethyl-2-amino-5,8-dimethoxytetralin hydrochloride;

(−)-N-ethyl-(2S)-2-amino-5,8-dimethoxytetralin hydrochloride;

N-methyl-2-amino-5-bromo-8-methoxytetralin hydrochloride;

N-methyl-2-amino-8-methoxy-5-thiomethyltetralin hydrochloride;

N-methyl-2-amino-5-ethoxy-8-methoxytetralin hydrochloride;

N-methyl-2-amino-6-bromo-5,8-dimethoxytetralin hydrochloride;

(−)-N-methyl-(2S)-2-amino-8-methoxytetralin and

N-methyl-2-amino-8-methoxytetralin hydrochloride.

Particularly preferred species of the Formula I for use in the method described above are (−)-N-methyl-(2S)-2-amino-5,8-dimethoxytetralin hydrochloride and (−)-N-methyl-(2S)-2-amino-8-methoxytetralin.

Another particularly preferred species of the Formula I for use in the method described above is (−)-N-methyl-(2S)-2-amino-8-methoxytetralin hydrochloride.

The invention further relates to the use of a compound of the Formula I for the preparation of a medicament for the treatment or prevention of movement disorders.

The invention further relates to a process for preparing a compound of the Formula I:

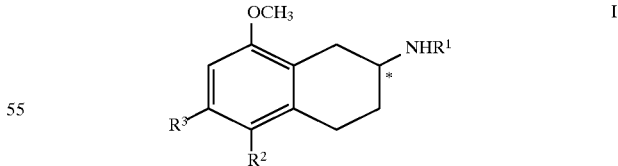

wherein:

$R^1$ is methyl or ethyl; $R^2$ is hydrogen, halogen, lower-alkoxy or thiolower-alkyl; $R^3$ is hydrogen, halogen, lower-alkoxy or lower-alkyl; and the chiral center * is in the (S)(−) form; or a pharmaceutically acceptable acid-addition salt thereof, with the proviso that when $R^2$ and $R^3$ are both hydrogen, $R^1$ must be methyl;

which comprises reacting a single enantiomer of a compound of the formula VIII:

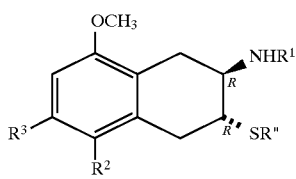

wherein R" is lower alkyl, with a reducing agent.

The term lower-alkyl as used herein means linear or branched hydrocarbon chains having from one to about four carbon atoms and thus includes methyl, ethyl, propyl, isopropyl, n-butyl, sec-butyl, tert-butyl and the like.

The term lower-alkoxy as used herein means linear or branched alkyloxy substituents having one to about four carbon atoms and thus includes methoxy, ethoxy, propoxy, isopropoxy, n-butoxy, sec-butoxy, tert-butoxy and the like.

The term halogen, halo, or halide as used herein means chlorine, bromine, iodine and fluorine.

The term thiolower-alkyl as used herein means linear or branched thioalkyl substituents having one to about four carbon atoms and thus includes thiomethyl (—SCH$_3$), thioethyl (—SCH$_2$CH$_3$), thiopropyl (—SCH$_2$CH$_2$CH$_3$), thioisopropyl (—CH(CH$_3$)$_2$), thiobutyl (—S(CH$_2$)$_3$CH$_3$), thiosec-butyl (—SCH(CH$_3$)CH$_2$CH$_3$), thio-tert-butyl (—SC(CH$_3$)$_3$) and the like.

While the compounds of the invention can be named as 2-aminotetralins or 2-amino-1,2,3,4-tetrahydronaphthalenes, throughout the specification they will be named as 2-aminotetralin derivatives and will be numbered as shown in the ring system illustrated hereinbelow.

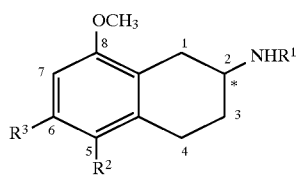

The synthesis of the compounds of the Formula I wherein the chiral center * is in the (R,S) form may be outlined as shown in Scheme A:

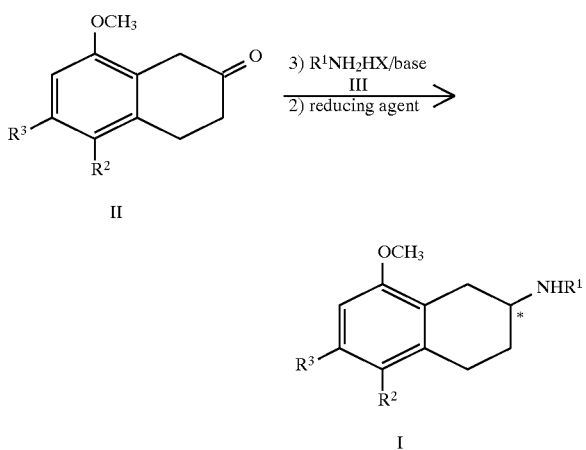

A molar excess of an amine salt of the Formula III, wherein X is a halogen, preferably chlorine, in an alcoholic solvent, preferably methanol, is treated with a suitably substituted 2-tetralone of the Formula II, at a temperature of about room temperature, followed by treatment with a suitable reducing agent, such as sodium cyanoborohydride, to afford the compounds of the Formula I.

Alternatively, the compounds of the Formula I wherein the chiral center * is the (R,S) form may be synthesized as showing in Scheme B:

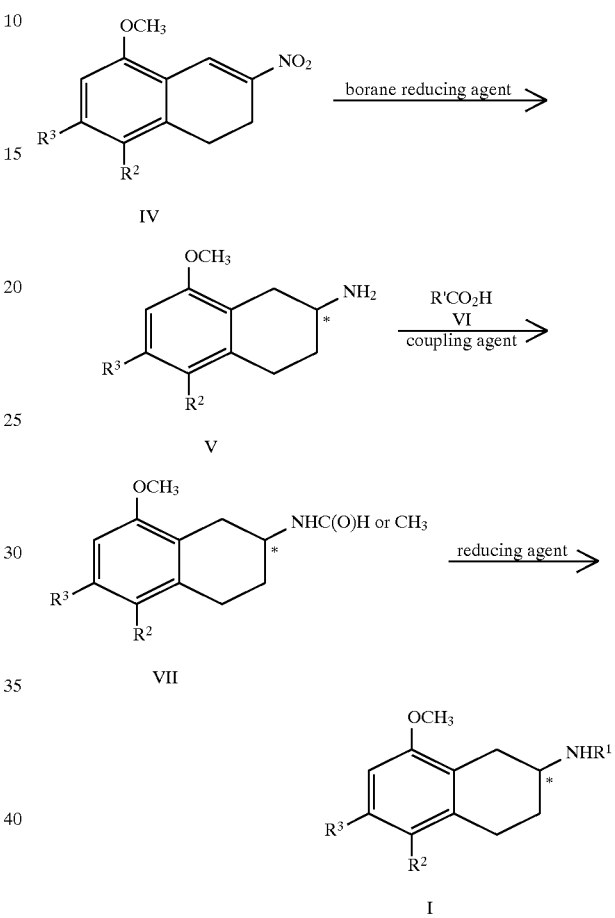

A molar excess of a borane reducing agent, prepared from a molar excess of sodium borohydride and a molar excess of boron trifluoride etherate, in a suitable organic solvent, such as tetrahydrofuran, at a temperature in the range of about 0° C. up to about room temperature, is treated with a solution of a 2-nitronaphthalene of the Formula IV in a suitable solvent, such as tetrahydrofuran, and the mixture is stirred at a temperature in the range of about room temperature up to the boiling point of the solvent used, preferably at the boiling point of the solvent used, to afford the 2-aminotetralins of the Formula V. Alternatively, the compounds of the Formula IV can be reduced with sodium borohydride to afford 2-nitrotetralins which in turn can be reduced with standard reducing agents to afford the 2-aminotetralin of the formula V. The compounds of the Formula V can then be added to a mixture of molar excess of an acid of the Formula VI, wherein R' is H or CH$_3$, and a coupling agent, such as 1,1-carbonyldiimidazole, in an appropriate organic solvent, such as tetrahydrofuran or a mixture of tetrahydrofuran and methylene chloride, at a temperature of about room temperature, to afford the compounds of the Formula VII. The compounds of the Formula VII in an appropriate organic solvent, such as tetrahydrofuran, can then be treated with a molar excess of a reducing agent, such as borane, at a temperature in the range of about 0° C. up to the boiling point of the solvent used, to afford the compounds of the Formula I.

Alternatively, the compounds of the Formula I may be synthesized as shown in Scheme C:

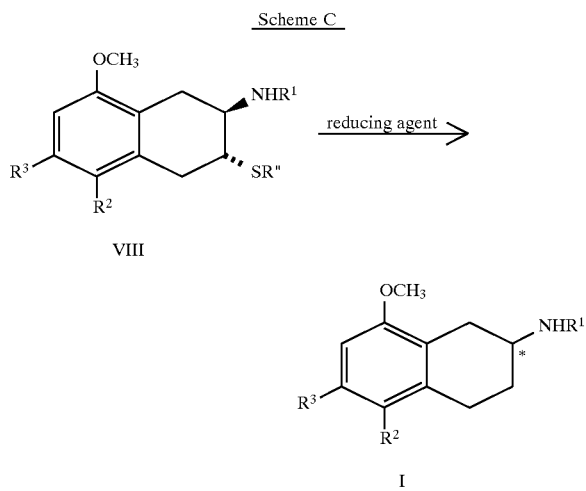

A mixture of a suitably substituted compound of the Formula VIII, wherein R" is lower-alkyl, preferably methyl, and a molar excess of a nickel chloride hydrate, preferably nickel chloride trihydrate, in an alcoholic solvent, such as methanol, at a temperature in the range of about 0° C. up to about room temperature, can be treated with a molar excess of a reducing agent, preferably sodium borohydride, to afford the compounds of the Formula I. While it will be appreciated that this process can be used to prepare all of the compounds of the Formula I, it is preferably used to prepare the compounds of the Formula I wherein $R^2$ is methoxy and $R^3$ is hydrogen.

It will be appreciated that the compounds of the Formula I possess an asymmetric carbon atom at the 2-position of the aminotetralin ring and are thus capable of existing (1) in the enantiomeric ((R) or (S)) form, or (2) in racemic (R,S) form (designated herein as the "racemic (R,S) form") or (3) as a mixture of the (R) form and the (S) form in any proportions (designated herein as the "(R,S) form"). Unless otherwise specified herein, the invention is intended to extend solely to (1) the (S) form and (2) mixtures of the (R) and (S) forms (the (R,S) form) but only to the extent that the proportion of the (S) form in the mixture is 50% or greater. The different enantiomeric forms may be separated one from the other by the following methods: (a) the separate enantiomers may be synthesized from chiral starting materials (e.g., the compounds of the Formula VIII can be separated into their separate enantiomers by chiral chromatography and the separate enantiomers can then be used to prepare the compounds of the Formula I as described in Scheme C or the compounds of the Formula XIV (see Scheme E) can undergo an enantioselective aziridination reaction followed by a reductive ring opening utilizing procedures similar to those described in J. Am. Chem. Soc. 1993, 115, 5328–5329 and J. Am. Chem. Soc. 1993, 115, 5326–5327 in order to prepare the compounds of the Formula I, or the separate enantiomers of the compounds of the Formula V or VII can be used to prepare the compounds of the Formula I as described in Scheme B), or (b) the (R,S) form or racemic (R,S) form may be resolved by conventional procedures which are well known in the art of chemistry such as chiral chromatography, fractional crystallization of diasteriomeric salts, enzymatic resolution and the like. It will also be appreciated that it is known from x-ray crystallographic studies that the (−)-enantiomers of 2-aminotetralins have the absolute S configuration (see Demarinis and Hiebe, J. Med. Chem. 1983, 26, 1215) and that the (+)-enantiomers of 2-aminotetralines have the absolute R configuration (see Karlsson et al., Acta Chemica Scandinavica 1988, B42, 231–236). Thus, the compounds of the instant invention which exist in the (S) form may also be designated as the (S)(−) form.

The compounds of Formula I are useful both in the free base form, and in the form of acid-addition salts, and both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The suitably substituted 2-tetralone derivatives of the Formula II, which are required for the synthesis of the compounds of the Formula I, can be prepared as described in Scheme D. A suitably substituted compound of the formula IX,

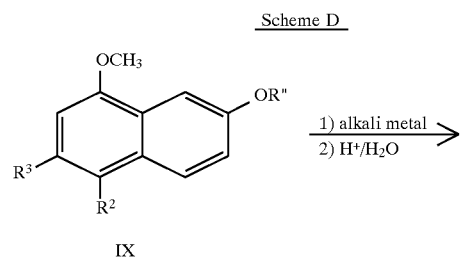

-continued
Scheme D

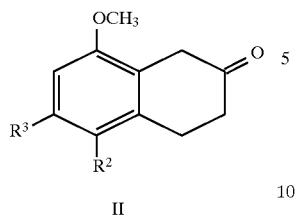

II wherein R" is lower-alkyl, preferably methyl, in an appropriate alcoholic solvent, such as ethanol, is treated with a molar excess of an alkali metal, preferably sodium, at a temperature in the range of about room temperature up to the boiling point of the solvent used, preferably at the boiling point of the solvent used, followed by treatment with water and an appropriate acid, preferably hydrochloric acid, at a temperature in the range of about room temperature up to the boiling point of the solvent used, preferably at the boiling point of the solvent used, to afford the compounds of the Formula II.

The suitably substituted 2-nitronaphthalenes of the Formula IV can be prepared as shown in Scheme E. A suitably substituted benzyl alcohol derivative of the Formula X, in an appropriate organic solvent, such as acetonitrile, is treated with a molar excess of an alkali metal halide, preferably sodium bromide, followed by treatment with a molar excess of an appropriate acid catalyst, preferably $BF_3 \cdot Et_2O$, to afford the compounds of the Formula XI wherein X is a halogen. Alternatively, the compounds of the Formula XI can be prepared by treating a compound of the Formula X, in the presence of an appropriate base, such as pyridine, in an appropriate organic solvent, such as diethyl ether, with a thionyl halide of the formula $SOX_2$ wherein X is a halogen, such as thionyl chloride, at a temperature of about room Scheme E

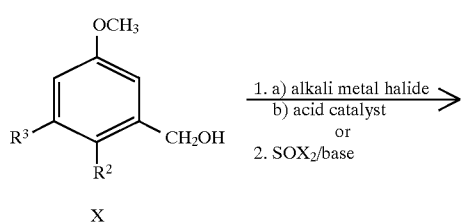

X

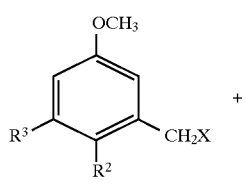

XI

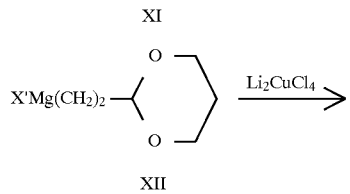

XII

-continued
Scheme E

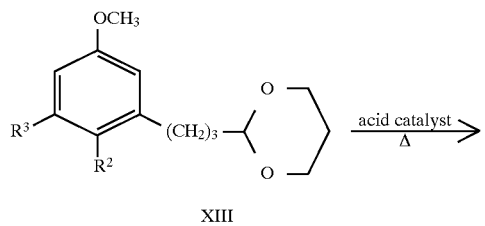

XIII

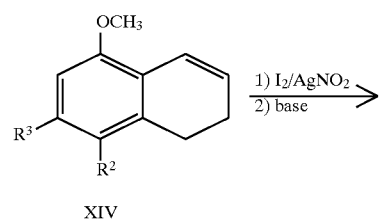

XIV

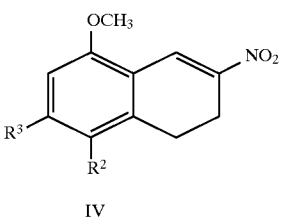

IV temperature. The compounds of the Formula XI can then be treated with a molar excess of magnesium halide of the Formula XII, wherein X' is a halogen, and a catalytic amount of $Li_2CuCl_4$, in an appropriate organic solvent, such as tetrahydrofuran, at a temperature in the range of about $-10°$ C. up to about room temperature, to afford the compounds of the Formula XIII. The compounds of the Formula XIII can then be treated with a catalytic amount of an acid catalyst, preferably p-toluenesulfonic acid monohydrate, in an appropriate organic solvent, such as toluene or ethanol, at a temperature in the range of about room temperature up to the boiling point of the solvent used, preferably at the boiling point of the solvent used, to afford the compounds of the Formula XIV. The compounds of the Formula XIV can then be treated with a molar excess of a mixture of iodine and silver nitrate, in an appropriate organic solvent, such as tetrahydrofuran, at a temperature of about room temperature, followed immediately by treatment with a molar excess of a suitable base, preferably pyridine, to afford the desired compounds of the Formula IV.

The compounds of the Formula XIV described hereinabove can alternatively be prepared as shown in Scheme F. A suitably substituted tetralone derivative of the Formula XV, Scheme F

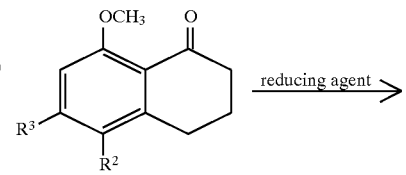

XV

-continued
Scheme F

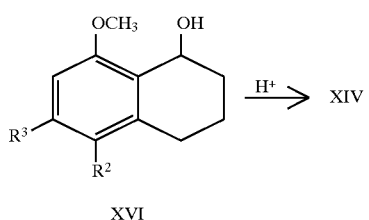

XVI in a suitable alcoholic solvent, such as ethanol, is treated with a molar equivalent of a reducing agent, preferably sodium borohydride, at a temperature of about room temperature, to afford the alcohols of the Formula XVI. The alcohols of the Formula XVI in an appropriate organic solvent, such as toluene, can then be treated with a catalytic amount of an acid catalyst, preferably p-toluenesulfonic acid, with the azeotropic removal of water, at a temperature of about the boiling point of the solvent used, to afford the desired compounds of the Formula XIV.

The compounds of the Formula VIII, which are useful as intermediates in the preparation of the compounds of the Formula I, can be prepared as shown in Scheme G following a procedure similar to that described in Trost et al., J. Am. Chem. Soc. 104, 3226 (1982). A molar excess of trimethyl-oxonium tetrafluoroborate in an appropriate organic solvent, such as acetonitrile, is treated with a sulfide of the formula, $(R'')_2S_2$ (XVIII) wherein R" is lower-alkyl, preferably

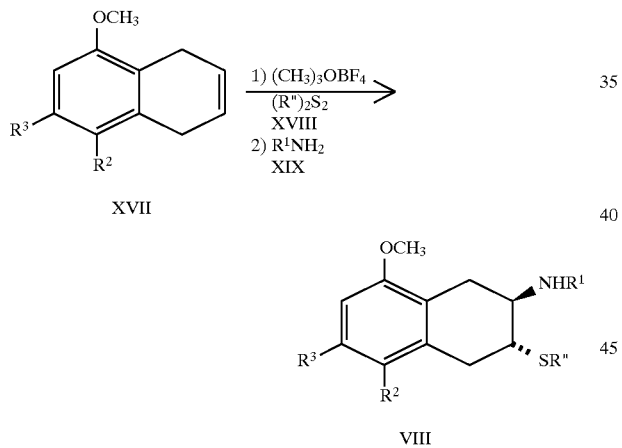

methyl, at a temperature in the range of about 0° C. up to about room temperature, followed by treatment of the mixture with an amine of the formula XIX, wherein $R^1$ is methyl or ethyl, at a temperature of about room temperature to afford the compounds of the Formula VIII. While it is appreciated that this procedure can be used to make all of the compounds of the Formula VIII, it is preferably used to make the compounds of the Formula VIII wherein $R^2$ is methoxy and $R^3$ is hydrogen.

Simple chemical tranformations which are conventional and well known to those in the art of chemistry can be used for effecting changes in the functional groups of the intermediate compounds of the invention, such as, for example, treating compounds of the Formula XIV wherein $R^2$ is halogen with lower-alkyl alkali metal, such as n-butyllithium followed by a lower-alkyl disulfide, i.e. $(CH_3)_2S_2$, to afford the corresponding compounds of the Formula XIV wherein $R^2$ is thiolower-alkyl.

The compounds of the Formulas III, VI, IX, X, XII, XV, XVII, XVIII and XIX are either commercially available, or they can be prepared by procedures known in the art, or by the procedures described hereinbelow in the examples.

The following examples will further illustrate the invention without, however, limiting it thereto. Unless stated otherwise:

(i) temperatures are given in degrees Celsius (°C.); operations were carried out at room or ambient temperature, that is, at a temperature in the range of 18°–25° C.;

(ii) evaporation of solvent was carried out using a rotary evaporator under reduced pressure (600–4000 pascals; 4.5–30 mm Hg;

(iii) flash chromatography was carried out on 40 µM silica gel, flash chromatography packing obtained from J. T. Baker; thin layer chromatography (TLC) was carried out on Analtech 0.25 mm silica gel GHLF plates (Art 21521), obtainable from Analtech, Newark, Del., USA;

(iv) the course of the reactions and the identity and homogenity of the products were assessed by one or more of thin layer chromatography (TLC), high pressure liquid chromatography (HPLC), or gas-liquid chromatography (GLC);

(v) melting points are uncorrected and (dec) indicates decomposition; the melting points given are those obtained for the materials prepared as described; polymorphism may result in isolation of materials with different melting points in some preparations;

(vi) the structures of the compounds of the invention were established by the mode of synthesis, and by one or more of micro analytical (elemental analysis) data, infrared, nuclear magnetic resonance (NMR) or mass spectroscopy;

(vii) yields and reaction times are given for illustration only;

(viii) chemical symbols have their usual meanings; the following abbreviations have the meanings indicated: v (volume), w (weight); mp (melting point), L [liter(s)], mL (milliliters), mmol (millimoles), h or hr [hour(s)], min [minute(s)], g or gm [gram(s)], mg [milligram(s)], bp [boiling point], mm [millimeters]; and (ix) solvent ratios are given in volume:volume (v/v) terms, unless indicated otherwise.

EXAMPLE 1

N-Methyl-2-amino-5,8-dimethoxytetralin Hydrochloride*

A 250 ml 3-necked flask equipped with a mechanical Teflon blade stirrer and a condenser fitted with a Drierite tube was charged with 7.1 gm (39 mmol) of nickel chloride trihydrate and 50 ml of methanol. To this green solution was added a solution of 1.30 gm (4.86 mmol) of trans N-methyl-2-amino-5,8-dimethoxy-3-thiomethyltetralin in 30 ml methanol, followed by cooling in an ice-salt bath. Sodium borohydride, 6.45 gm (170 mmol), was added portionwise over 45 minutes. The bath was then removed and the black heterogeneous solution was stirred overnight (22 hours). Tlc analysis (silica gel; $NH_4OH$:methanol: $CH_2Cl_2$, 1:10:89) of an aliquot, diluted with ethyl acetate, indicated a major component at $R_f$ 0.42 and absence of starting amine ($R_f$ 0.72). The content was transferred with methanol to a single necked one liter flask and the solvent was removed in vacuo using a rotary evaporator until a solid residue remained. This residue was triturated with 100 ml water, a trubor stirrer with teflon blade was attached and 200 ml of ethyl acetate was added. After stirring for 2 hours, the heterogeneous solution was filtered through CELITE®, the cake being washed well with ethyl acetate. The ethyl acetate extract was washed with water, brine and dried ($MgSO_4$). Filtration and removal of solvent in vacuo using a rotary evaporator left a residue which was transferred with $CH_2Cl_2$ to a smaller flask. The solvent was removed as above and the residue was further heated in a kugelrohr to 70° C. at 15 mm Hg to yield 0.93 gm. This material was then kugelrohr distilled at 0.01 mm Hg to yield 0.81 gm (75%) of a colorless oil, bp 105°–115° C. (air bath temperature).

This oil was dissolved in ether and treated with ethereal HCl to give a white precipitate which was collected by filtration and air dried (0.88 gm). This salt was dissolved in 40 ml hot isopropanol, concentrated to 10 ml and left at room temperature. The resulting solid was collected by filtration, washed with ether and dried in a drying pistol over refluxing methanol at 0.01 mm Hg to yield 0.71 gm (55%), mp 221°–222° C.

[*Described by D. B. Rusterholz et al., in J. Med. Chem (1976), 19 99]

a. The starting trans N-methyl-2-amino-5,8-dimethoxy-3-thiomethyltetralin was prepared as follows: A dry 3-necked 100 ml round-bottom flask equipped with a condenser bearing a nitrogen inlet, a septum on one neck and a magnetic stirring bar was charged with 2.0 gm (13.5 mmol) trimethyloxonium tetrafluoroborate. Acetonitrile, 11 ml (dried with molecular sieves), was added and the stirred solution was cooled in an ice bath. By syringe, 1.3 ml (12.6 mmol) of dimethyl disulphide was added. The solution was stirred for 20 minutes in the cold, for 40 minutes at room temperature and was then recooled in the ice bath. 5,8-Dimethoxy-1,4-dihydro-naphthalene*, 2.40 gm (13.52 mmol), was added as a solid followed by dilution with 6 ml acetonitrile. After 15 minutes, the solution was allowed to stir at room temperature for one hr and was then recooled in an ice bath. Methylamine, 8 ml (40% aqueous solution), was then added by pipette and the solution was stirred overnight (20 hr) at room temperature. The contents of the flask was transferred to a separatory funnel with ethyl acetate. The ethyl acetate extract was washed several times with water, then brine, and dried with magnesium sulphate. Filtration and removal of solvent at reduced pressure using a rotary evaporator left 3.38 gm of a solid. TLC analysis on silica gel plates using methanol:methylene chloride (5:95) with UV and iodine detection indicated the product with $R_f$ 0.50 with minor impurities with lower $R_f$'s as well as impurities near the solvent front. This material was purified by column "flash" chromatography (Baker 40 μm silica gel) using 50 gm of silica gel and eluting with methanol: methylene chloride (3:97). The fractions containing the pure material were combined and the solvent was removed on a rotary evaporator to yield 1.59 gm, mp 82°–84° C.

[* Prepared according to procedure of J. Alexander and L. A. Mitscher, Tetrahedron Letters (1978) 3403]

Trans N-methyl-2-amino-5,8-dimethoxy-3-thiomethyltetralin: Alternate method of isolation.

The crude material resulting from the azasulphenylation of 2.40 gm of 5,8-dimethoxy-1,4-dihydronaphthalene described in example 1a was dissolved in 40 ml ethanol and treated with excess ethanolic HCl. The solvent was removed in vacuo using a rotary evaporator to give a solid residue which was triturated with 200 ml ether and collected by filtration. This hydrochloride salt was added to water and treated with ethyl acetate and 2N NaOH. The ethyl acetate extract was washed with water, brine and dried (magnesium sulphate). Filtration and removal of solvent in vacuo using a rotary evaporator gave a solid, 2.35 gm (71%).

EXAMPLE 2

(−)N-Methyl-(2S)2-amino-5,8-dimethoxytetralin Hydrochloride

Using the procedure as described in Example 1, 0.67 gm (2.53 mmol) of (−)N-methyl-(2R)2-amino-5,8-dimethoxy-(3R)3-thiomethyltetralin in 35 ml methanol was added to 3.70 gm (20 mmol) $NiCl_2 \cdot 3\ H_2O$ in 35 ml methanol and reduced with 4.00 gm (105 mmol) of $NaBH_4$. The material from the ethyl acetate extract was transferred to a smaller flask with ether and concentrated. Kugelrohr distillation gave 0.337 gm, bp 95°–105° C. (air bath temperature) at 0.005 mm Hg. This oil was dissolved in ether and treated with ethereal HCl to give a white precipitate which was collected by filtration and air dried to yield 0.40 gm. This salt was dissolved in 25 ml hot isopropanol and concentrated to 9 ml. The resulting solid was collected by filtration and dried in a drying pistol over refluxing methanol to give 0.348 gm, mp 228°–228.5° C.; $[\alpha]_D^{22}$ −72° (c=1, methanol).

a. (−)N-Methyl-(2R)2-amino-5,8-dimethoxy-(3R)3-thiomethyltetralin

The starting (−)N-Methyl-(2R)2-amino-5,8-dimethoxy-(3R)3-thiomethyltetralin was obtained as the second material to elute on subjecting the racemic material in Example 1a to preparative Chiralcel OD HPLC resolution using a hexane/ethanol mixture. The enantiomeric purity was determined on an analytical scale using 99:1 (v/v) hexane:ethanol, a flow rate of 1 ml per minute and detection at 235 nm. The solution containing this isomer was concentrated using a rotary evaporator to give 0.63 gm of a white solid, mp 86.5°–88° C.; $[\alpha]_D^{22}$ −138° (c=1.04, methanol). A solution of 0.58 gm in ether was treated with ethereal HCl to give a white precipitate which was collected by filtration and dried overnight in a drying pistol over refluxing methanol at 0.005 mm Hg to yield 0.62 gm; mp 256°–257° C.; $[\alpha]_D^{22}$ −93° (c=0.875, methanol).

EXAMPLE 3

(+)N-Methyl-(2R)2-amino-5,8-dimethoxytetralin Hydrochloride

Using the procedure as described in example 1, 0.79 gm (3.0 mmol) of (+)N-methyl-(2S)2-amino-5,8-dimethoxy-(3S)3-thiomethyltetralin in 35 ml methanol was added to 4.33 gm (24 mmol) $NiCl_2 \cdot 3\ H_2O$ in 35 ml methanol and reduced with 4.00 gm (105 mmol) of $NaBH_4$. The material from the ethyl acetate extract was transferred to a smaller flask with ether and concentrated to give 0.35 gm. Kugelrohr distillation gave 0.33 gm, bp 90°–110° C. (air bath temperature) at 0.005 mm Hg. This oil was dissolved in ether and treated with ethereal HCl to give a white precipitate which was collected by filtration and air dried to yield 0.34 gm. Recrystallization from isopropanol and drying in a drying pistol over refluxing methanol gave 0.237 gm, mp 226.5°–227° C. An aliquot was taken to the base which was homogeneous by tlc (silica gel, 1:10:89 $NH_4OH$:methanol:$CH_2Cl_2$); $[\alpha]_D^{22}$ +75.2° (c=0.585, methanol).

a. (+)N-Methyl-(2S)2-amino-5,8-dimethoxy-(3S)3-thiomethytetralin

The starting (+)N-Methyl-(2S)2-amino-5,8-dimethoxy-(3S)3-thiomethytetralin was obtained as the first material to elute on subjecting the racemic material in Example 1a to preparative Chiralcel OD HPLC resolution using hexane/ethanol. The enantiomeric purity was determined on an analytical scale using 99:1 (v/v) hexane:ethanol, a flow rate of 1 ml per minute and detection at 235 nm. The solution containing this isomer was concentrated using a rotary evaporator to give 0.70 gm of a white solid, mp 86.5°–88° C.; $[\alpha]_D^{22}$ +136° (c=0.875, methanol). A solution of 0.66 gm in ether was treated with ethereal HCl to yield a flocculant precipitate which was collected by filtration. This material was dried overnight in a drying pistol over refluxing methanol at 0.010 mm Hg to yield 0.71 gm, mp 257°–257.5° C.; $[\alpha]_D^{22}$ +94° (c=1.00, methanol).

EXAMPLE 4

N-Ethyl-2-amino-5,8-dimethoxytetralin Hydrochloride

Using the procedure as described in Example 1, 0.81 gm (2.88 mmol) of trans N-ethyl-2-amino-5,8-dimethoxy-3-thiomethyltetralin in 35 ml methanol was added to 4.23 gm (23 mmol) $NiCl_2 \cdot 3 H_2O$ in 50 ml methanol and reduced with 3.8 gm (100 mmol) of $NaBH_4$. The material from the ethyl acetate extract was transferred to a smaller flask with ether and concentrated to give 0.59 gm. Kugelrohr distillation gave 0.53 gm (79%) of a colorless liquid, bp 95°–105° C. (air bath temperature) at 0.005 mm Hg; tlc on silica gel (1:10:89 $NH_4OH:CH_3OH:CH_2Cl_2$) $R_f$ 0.48. This oil was dissolved in ether and treated with ethereal HCl to give a white precipitate which was collected by filtration and dried in a drying pistol over refluxing methanol to yield 0.53 gm, mp 207°–208° C.

a. The starting trans N-ethyl-2-amino-5,8-dimethoxy-3-thiomethyltetralin was prepared as follows: As in Example 1a, 2.41 gm (12.6 mmol) of 5,8-dimethoxy-1,4-dihydronaphthalene was azasulphenylated using 2.00 gm (13.5 mmol) of trimethyloxonium tetrafluoroborate, 1.13 ml (12.6 mmol) of dimethyl disulphide and 9 ml of 70% aqueous ethylamine. The crude material obtained by ethyl acetate extraction was dissolved in 40 ml ethanol and 20 ml ethanolic HCl and the solvent was removed in vacuo using a rotary evaporator. The residue was partitioned between ether and water. Treatment of the aqueous phase with $NH_4OH$ resulted in the separation of an oil which was induced to crystallize by scratching. This solid was collected by filtration and dried to yield 2.32 gm, mp 91°–92° C.; tlc on silica gel (10:90 $MeOH:CH_2Cl_2$), $R_f$ 0.60.

EXAMPLE 5

(−)N-Ethyl-(2S)2-amino-5,8-dimethoxytetralin Hydrochloride

Using the procedure as described in Example 1, 0.92 gm (3.3 mmol) of trans(−)N-ethyl-(2R)2-amino-5,8-dimethoxy-(3R)3-thiomethyltetralin in 50 ml methanol was added to 4.84 gm (26.4 mmol) $NiCl_2 \cdot 3 H_2O$ in 45 ml methanol and reduced with 4.4 gm (125 mmol) of $NaBH_4$. The material from the ethyl acetate extract was transferred to a smaller flask with ether and concentrated to give 0.59 gm. Kugelrohr distillation gave 0.52 gm (77%) of a colorless liquid, bp 95°–105° C. (air bath temperature) at 0.005 mm Hg; tlc on silica gel (1:10:89 $NH_4OH:CH_3OH:CH_2Cl_2$) $R_f$ 0.46. This oil was dissolved in ether and treated with ethereal HCl to give a white precipitate which was collected by filtration and dried in a drying pistol over refluxing methanol to yield 0.52 gm, mp 227°–229° C.; $[\alpha]_D^{22}$ −68° (c=0.56, methanol).

a. (−)N-ethyl-(2R)2-amino-5,8-dimethoxy-(3R)3-thiomethytetralin

The starting (−)N-ethyl-(2R)2-amino-5,8-dimethoxy-(3R)3-thiomethytetralin was obtained as the second material to elute on subjecting the racemic material in Example 4a to preparative Chiralcel OD HPLC resolution using hexane/ethanol. The enantiomeric purity was determined on an analytical scale using 99:1 (v/v) hexane:ethanol, a flow rate of 1 ml per minute and detection at 220 nm. The solution containing the second eluting isomer was concentrated using a rotary evaporator to give 1.01 gm of a white solid which was again subjected to preparative chiracel OD HPLC for purification to homogeniety, yielding 0.77 gm.

EXAMPLE 6

N-Methyl-2-amino-5-bromo-8-methoxytetralin Hydrochloride

A solution of N-formyl-2-amino-5-bromo-8-methoxytetralin, (0.59 g, 2.1 mmol) in dry THF (20 ml), was treated with borane in THF (6.5 ml of 1.0M solution) at 0° C. under nitrogen and refluxed overnight. After 25 hours, the solution was cooled to room temperature and the excess borane was destroyed by careful addition of water. After 30 min, 5 ml of 6N HCl was added in portions and the mixture was refluxed for 1 hour. After cooling to room temperature, the solvent was evaporated and the residue was treated with a solution of 10 ml conc. $NH_4OH$ in 100 ml 1N NaOH and extracted with ether. The ether layer was washed with 1N NaOH, water, brine, dried over $MgSO_4$, filtered, and evaporated to yield crude amine (0.573 g). The crude material was purified by kugelrohr distillation (110° C., 0.04 mmHg) to yield a colorless syrup (0.468 g, 84%); tlc (silica gel, 1:9 $MeOH:CH_2Cl_2$), $R_f$ 0.25. This material was treated with ethereal HCl to give a solid which was collected by filtration and dried in vacuo to yield 0.373 g, (70%); mp 227°–229° (browning 218°–227°).

The starting materials were obtained as follows:

a. 2-Bromo-5-methoxybenzyl Alcohol

A solution of 2-bromo-5-methoxybenzoic acid (10.00 g, 43.3 mmol) in dry THF (40 ml) was treated with borane in THF (65 ml of 1.0M solution, 65 mmol) at room temperature under nitrogen. After stirring for 4 h, no starting material was detectable by tlc. Excess borane was quenched by careful addition of water over 30 min, and the solvent was evaporated under reduced pressure. The residue was partitioned between ether and 5% $Na_2CO_3$. The ether layer was washed with 5% $Na_2CO_3$, water, and brine, and dried over $MgSO_4$. Filtration and removal of solvent left a colorless oil which solidified (9.11 g, 97%); tlc (silica gel, $CH_2Cl_2$, $R_f$ 0.25). This material was used without further purification.

b. 2-Bromo-5-methoxybenzyl Bromide*

Sodium bromide (9.06 g, 84.0 mmol) was added to a solution of 2-bromo-5-methoxy benzyl alcohol (9.11 g, 42.0 mmol) in dry acetonitrile (65 ml) at room temperature under $N_2$. The resulting suspension was treated dropwise with a solution of $BF_3$-etherate (10.3 ml, 11.9 g, 84.0 mmol) in 10 ml $CH_3CN$, then heated to reflux. After 23 h, the contents were cooled, filtered and evaporated. The residue was partitioned between ether and sat. $NaHCO_3$. The ether layer was washed with 5% $NaHCO_3$, 5% $NaHSO_3$, and brine, and dried over $MgSO_4$. Filtration and removal of solvent gave the crude bromide (11.51 g) as a pale yellow solid (caution: lachrymator.). The crude bromide was kugelrohr distilled (75°–90° C., 0.03 mmHg) to yield 10.60 g of white solid which was further purified by column chromatography (160 g silica gel, 100% $CH_2Cl_2$ as eluent, flash conditions) to yield 7.93 gm (67%) as a white crystalline solid, mp 89.5°–91°. Tlc (silica gel, $CH_2Cl_2$), $R_f$ 0.75.

*(procedure from Mandal, A. K.; Mahajan, S. W. *Tetrahedron Letters*, 1985, 26, 3863.)

c. 2-[3-(2-Bromo-5-methoxyphenyl)propyl]-1,3-dioxane

A solution of 2-(2-bromoethyl)-1,3-dioxane (3.41 ml, 4.88 g, 25.0 mmol) in dry THF (15 ml) was slowly added to dry magnesium turnings (0.67 g, 27.5 mmol) and ~10 mg iodine at room temperature under $N_2$. After heat evolved and the iodine color vanished, the contents were heated to reflux and the remainder of the bromide solution was added dropwise over 10 min. After 2 h reflux, the alkylmagnesium-bromide solution was cooled to room temperature and transferred via syringe to a solution of 2-bromo-5-methoxybenzyl bromide (3.50 g, 12.5 mmol) in 20 ml dry THF. The contents were cooled to –10° with ice-salt, treated with $Li_2CuCl_4$ in THF (0.45 ml of 0.1M solution), and allowed to stir at room temperature overnight for convenience. After 19 h, the solvent was evaporated and the residue partitioned between ether and 5% $NH_4Cl$. The ether layer was washed with 5% $NH_4Cl$, water, and brine, then dried over $MgSO_4$, filtered, and evaporated to yield 4.59 g of a pale yellow oil. The crude material was purified by column chromatography (140 g silica gel, 50% ether/petroleum ether as eluent) under "flash" conditions to yield 2.31 gm (58%) of the dioxane as a colorless oil; tlc (silica gel, 50% ether/petroleum ether) $R_f$ 0.48. A dimeric by-product, 1,2-bis(2-bromo-5-methoxyphenyl)ethane, was obtained as a white solid (1.02 g, 41%); mp 98°–101°. TLC (silica gel, 50% ether/petroleum ether) $R_f$ 0.63.

d. 5-Bromo-8-methoxy-3,4-dihydronaphthalene

A solution of dioxane 6c (2.26 g, 7.17 mmol) and p-toluenesulfonic acid monohydrate (~20 mg) in dry toluene (15 ml) was heated to reflux. The reaction was monitored by TLC (silica gel, $CH_2Cl_2$) and 10–20 mg portions of pTsOH were added every few hours until no detectable change in the relative amounts of starting material ($R_f$ 0.45) and product ($R_f$ 0.80) could be detected by TLC. After refluxing 51 hours, the contents were cooled to room temperature, diluted with ether, and washed with 5% $NaHCO_3$, water, brine, then dried over $MgSO_4$, filtered, and evaporated to yield 1.87 gm of the crude olefin. The crude material was kugelrohr distilled (80° C., 0.02 mmHg) to yield a colorless oil, 1.21 gm (70%); TLC (silica gel, $CH_2Cl_2$) $R_f$ 0.80.

e. 5-Bromo-3,4-dihydro-8-methoxy-2-nitronaphthalene*

A suspension of iodine (1.96 g, 7.73 mmol) and silver nitrite (1.18 g, 7.73 mmol) in dry THF (20 ml, distilled from Na) was stirred vigorously for 20 min at room temperature under nitrogen. A solution of 5-bromo-8-methoxy-3,4-dihydro naphthalene (0.88 g, 3.68 mmol) in 15 ml THF was added in one portion, followed quickly by dry pyridine (1.25 ml, 15.5 mmol). After stirring 5 min, the contents were filtered, triethylamine (2 ml) added to the filtrate and the solvent evaporated under reduced pressure. The residue was diluted with dry $CH_2Cl_2$, triethylamine (4 ml) added, and the resulting solution allowed to sit at room temperature for 2 h. The solvent was evaporated, the residue taken up in ethyl acetate, washed with water, 1.5N HCl, 5% $Na_2CO_3$, water, and brine, then dried over $MgSO_4$, filtered, and evaporated to yield 1.72 g of a dark brown oil. The crude material was purified by column chromatography (80 g silica gel), where the product was visible as an orange band, eluting with $CH_2Cl_2$ under flash conditions to yield the nitroalkene as a yellow solid (0.74 g, 71%); tlc (silica gel, $CH_2Cl_2$) $R_f$ 0.75.

* See general procedure in Jew et al., *Chemistry Letters*, 1747 (1986).

f. 2-Amino-5-bromo-8-methoxytetralin

Boron trifluoride etherate (2.5 ml, 20.0 mmol) was added dropwise via an addition funnel to a stirred suspension of sodium borohydride (0.66 g, 17.5 mmol) in dry THF (10 ml, distilled from Na) at 0° C. The resulting slurry was stirred at 0° C. for 30 min, then allowed to warm to room temperature. After 30 min, a solution of the above nitroalkene (0.86 g, 3.0 mmol) in THF (15 ml) was added dropwise and the contents refluxed overnight. After cooling to room temperature, the excess borane was destroyed by careful addition of water. After 1 hour ~7 ml of 6N HCl was added in portions and the mixture refluxed for 3 h. After cooling to room temperature, the solvent was evaporated and the residue treated with a solution of 10 ml conc. $NH_4OH$ in 100 ml 1N NaOH and extracted with ether. The ether layer was washed with 1N NaOH, water, brine, dried over $MgSO_4$, filtered, and evaporated to yield crude amine (0.702 g). The crude material was purified by kugelrohr distillation (120° C., 0.05 mmHg) to give a waxy solid (0.552 g, 71%); tlc (silica gel, 1:9 $MeOH:CH_2Cl_2$) $R_f$ 0.20. A portion of this amine (0.250 g, 0.97 mmol) was treated with ethereal HCl, the white solid was collected by filtration and dried in vacuo to yield the hydrochloride (0.197 g, 70%); mp>280° (browning 200°–280°).

g. N-formyl-2-amino-5-Bromo-8-methoxytetralin

To a solution of formic acid (98%, 0.09 ml, 2.4 mmol) in dry THF (5 ml, distilled from Na) at room temperature was added carbonyl duimidazole (0.38 g, 2.4 mmol) in one portion. After stirring 30 min, a solution of 2-amino-5-bromo-8-methoxytetralin (0.55 g, 2.15 mmol) in 20 ml THF was added dropwise, and the resulting solution was stirred overnight for convenience. After 18 hours, the solvent was evaporated and the residue was partitioned between water and ether. The organic layer was washed with water, brine, dried over $MgSO_4$, filtered, and evaporated to yield crude amide (0.591 g, 97%); tlc (silica gel, 1:9 $MeOH:CH_2Cl_2$), $R_f$ 0.65. This material was used without further purification.

EXAMPLE 7

N-Methyl-2-amino-5-ethoxy-8-methoxytetralin Hydrochloride

As in Example 6, N-formyl-2-amino-5-ethoxy-8-methoxytetralin, 450 mg (1.81 mmol), in 20 ml THF was reduced with 10 ml of 1.0M borane in THF by heating to reflux for 24 hr. An ethyl acetate extraction yielded 410 mg of a brown oil which was kugelrohr distilled to give 320 mg (75%) of a colorless oil, bp 100°–110° C. (air bath temperature) at 0.010 mm Hg. This oil, 310 mg, was dissolved in ether and treated with ethereal HCl to give a white precipitate which was collected by filtration and dried in a drying pistol over refluxing methanol at 0.01 mm Hg to yield 315 mg, mp 229°–231° C.

The starting materials were obtained as follows:

a. 5-Ethoxy-8-methoxy-3,4-dihydronaphthalene

A solution of 1.34 gm (6.10 mmol) of 5-ethoxy-8-methoxy-1-tetralone* in 30 ml ethanol was treated with 0.23 gm (6.10 mmol) $NaBH_4$. After 2.5 hr, tlc analysis indicated the absence of ketone and the solvent was removed in vacuo. The residue was partitioned between water and ether which was then dried ($MgSO_4$). Filtration and removal of solvent gave 1.21 gm of a yellow oil, homogeneous by tic (silica gel, ether), $R_f$ 0.64. A solution of this alcohol in 30 ml toluene was placed in a flask equipped with a Dean-Stark trap and condenser. Addition of a catalytic amount of p-toluene sulphonic acid followed by refluxing for 1 hr resulted in complete dehydration (tlc). The cooled solution was treated with 10 ml of saturated $Na_2CO_3$ solution, stirred and diluted with ether. The organic extract was washed with water and brine and dried ($MgSO_4$). Filtration and removal of solvent in vacuo gave a residue which was kugelrohr distilled, bp 90° C. (air bath temperature) at 0.005 mm Hg, to give 1.08 gm of a white solid, mp 59°–60° C.

* D. W. Johnson and L. H. Mander, Aust. J. Chem., 1978, 31, 1561.

b. 5-Ethoxy-8-methoxy-2-nitro-3,4-dihydronaphthalene

As in Example 6e a solution of 1.62 gm (7.94 mmol) of 5-ethoxy-8-methoxy-3,4-dihydronaphthalene in 20 ml THF was nitrated using 2.45 gm (15.88 mmol) silver nitrite and 4.03 (15.88 mmol) iodine in 30 ml THF, 2.5 ml pyridine and (sequentially) 4.0 and 8.0 ml triethylamine to yield a dark oil which solidified (2.52 gm). Purification by chromatography (80 gm silica gel and elution with methylene chloride) gave 1.23 gm (62%) of a yellow solid, mp 90°–92° C.

c. 2-Amino-5-ethoxy-8-methoxytetralin

As in Example 6f, 5-ethoxy-8-methoxy-2-nitro-3,4-dihydronaphthalene, 1.15 gm (4.62 mmol), in 25 ml THF was reduced with 0.90 gm (24 mmol) $NaBH_4$ in 25 ml THF and 3.42 ml (27.7 mmol) boron trifluoride etherate. Ethyl acetate extraction gave 1.20 gm. Purification by chromatography on silica gel (30 gm), eluting first with 10:90 and then 25:75 $CH_3OH:CH_2Cl_2$, gave 414 mg (41%) of an oil, homogeneous by tlc.

d. N-Formyl-2-amino-5-ethoxy-8-methoxytetralin

As in example 6g, 2-amino-5-ethoxy-8-methoxytetralin 408 mg (1.84 mmol) in 20 ml THF, was formylated with 360 mg (2.21 mmol) carbonyl dimidazole in 10 ml THF and 102 mg (2.21 mmol) formic acid in 3 ml THF. After stirring overnight, tlc analysis (silica gel; 10:90 $CH_3OH:CH_2Cl_2$) indicated a major component, Rf 0.53, and absence of starting amine, Rf 0.06. The residue obtained on removal of solvent was dissolved in ethyl acetate, washed with 3N HCl, $Na_2CO_3$ solution, brine and dried ($MgSO_4$). Filtration and removal of solvent in vacuo left an off-white solid, 460 mg (100%).

EXAMPLE 8

N-Methyl-2-amino-8-methoxy-5-thiomethyltetralin Hydrochloride

As in Example 6, N-formyl-2-amino-8-methoxy-5-thiomethyltetralin, 495 mg (1.97 mmol), in 20 ml THF was reduced with 9 ml of 1.0M borane in THF by heating to reflux for 24 hr. An ethyl acetate extraction yielded 460 mg of a yellow oil which was kugelrohr distilled to give 364 mg of a colorless oil, bp 120° C. (air bath temperature) at 0.010 mm Hg, homogeneous by tlc (silica gel; 1:5:94 $NH_4OH:CH_3OH:CH_2Cl_2$) $R_f$ 0.25. This oil, 358 mg, was dissolved in ether and treated with ethereal HCl to give a white precipitate which was collected by filtration and dried in a drying pistol over refluxing methanol at 0.05 mm Hg to yield 364 mg, mp 229°–230° C.

The starting materials were obtained as follows:

a. 8-Methoxy-5-thiomethyl-3,4-dihydronaphthalene

A dry 3-necked flask equipped with a magnetic stirring bar and condenser with a nitrogen inlet was charged with 2.19 gm (9.16 mmol) of 5-bromo-8-methoxy-3,4-dihydronaphthalene (prepared according to Example 6d) in 25 ml dry THF and the solution was cooled to −76° C. n-Butyllithium, 4.4 ml (11.0 mmol) of a 2.5M THF solution, was added using a syringe. After 90 minutes dimethyl disulphide, 3.0 ml (27 mmol), was added and the reaction mixture was allowed to warm to room temperature and stirred for 18 hr. The reaction was quenched with water and extracted twice with ether. The ether extract was washed with water, brine, dried ($MgSO_4$), filtered and concentrated in vacuo to yield 1.73 gm of a yellow oil. Tlc (silica gel; $CH_2Cl_2$) indicated a single component at $R_f$ 0.72. Kugelrohr distillation at 85°–95° C. (air bath temperature) at 0.01 mm Hg gave 1.69 gm.

b. 8-methoxy-2-nitro-5-thiomethyl-3,4-dihydronaphthalene

As in Example 6e, a solution of 845 mg (4.10 mmol) of 8-methoxy-5-thiomethyl dihydronaphthalene in 11 ml THF was nitrated using 1.26 gm (8.2 mmol) silver nitrite and 2.08 gm (8.2 mmol) iodine in 20 ml THF, 1.3 ml pyridine and (sequentially) 2 and 4 ml triethylamine to yield 1.05 gm of a solid. A second experiment as above gave 1.13 gm for a combined yield of 2.18 gm which was purified by column chromatography using 80 gm of silica gel and eluting with methylene chloride. The fractions containing the pure material were combined to give 1.24 gm of a yellow solid, mp 96°–97° C.

c. 2-Amino-8-methoxy-5-thiomethyltetralin*

As in example 6f, 8-methoxy-2-nitro-5-thiomethyl-3,4-dihydronaphthalene, 1.20 gm (4.8 mmol), in 15 ml THF was reduced with 0.94 gm (25 mmol) $NaBH_4$ in 25 ml THF and 3.55 ml (28.6 mmol) boron trifluoride etherate. The ethyl acetate extract gave 1.21 gm which was purified by silica gel column chromatography using 30 gm of silica gel and eluting with methylene chloride, 10:90 $CH_3OH:CH_2Cl_2$ and then 20:80 $CH_3OH:CH_2Cl_2$. The fractions containing the product were combined and freed from solvent to yield 460 mg; tlc analysis (silica gel; 1:5:94 $NH_4OH:CH_3OH:CH_2Cl_2$), $R_f$ 0.32.

* [See R. M. DeMarinis et al, J. Med. Chem (1982) 25, 136].

d. N-Formyl-2-amino-8-methoxy-5-thiomethyltetralin

Following a procedure similar to that discussed in Example 6g but adding formic acid to carbonyl diimidazole rather than carbonyl diimidazole to formic acid, 2-amino-8-methoxy-5-thiomethyltetralin, 451 mg (2.02 mmol) in 20 ml THF, was formylated with 393 mg (2.42 mmol) carbonyl dimidazole in 10 ml THF and 112 mg (2.42 mmol) formic acid in 4 ml THF. After stirring overnight, tlc analysis (silica gel; 10:90 $CH_3OH:CH_2Cl_2$) indicated a major component, $R_f$ 0.65, and absence of starting amine, $R_f$ 0.07. The residue obtained on removal of solvent was dissolved in ethyl acetate, washed with 3N HCl, $Na_2CO_3$ solution, brine and dried ($MgSO_4$). Filtration and removal of solvent in vacuo left a cream-colored solid, 520 mg.

EXAMPLE 9

N-Methyl 2-amino-8-methoxytetralin Hydrochloride*

Following procedure similar to that described by R. Borsch, Organic Synthesis VI, p449, a 250 ml 3-necked round bottomed flask equipped with a magnetic stirring bar, addition funnel and Dry Ice condenser protected with a Drierite tube was charged with 1.40 gm (20.7 mmol) methylamine hydrochloride and 15 ml methanol. Potassium hydroxide (85%), 0.40 gm (6.0 mmol), was added and the solution was stirred for 20 minutes. Using the addition funnel a solution of 2.80 gm (15.9 mmol) of 8-methoxy-2-tetralone in 8 ml methanol was added. After 20 minutes $NaBH_3CN$, 0.42 gm (6.68 mmol), in methanol was added via the addition funnel. After 3 hr, tlc analysis (silica gel; $CH_2Cl_2$) indicated the absence of starting ketone. The reaction mixture was treated with 1.5 gm of KOH (85%), stirred for 30 minutes, filtered through CELITE® and then concentrated in vacuo using a rotary evaporator. The residue was partitioned between ethyl acetate and 1N NaOH and the organic extract was washed with brine and dried ($MgSO_4$). Filtration of the dark solution and removal of solvent in vacuo left a dark solid which was kugelrohr distilled, bp 85°–100° C. (air bath temperature) at 0.15 mm Hg, to give an oil, 1.20 gm (37%). This oil in ether was treated with ethereal HCl to form a gummy precipitate which on stirring formed a fine solid which was collected by filtration, 1.32 gm. After being dried in a drying pistol at 60° C. and 0.20 mm Hg, this material exhibited mp 139°–140° C.

* See Arvidsson et al., J. Med. Chem., 1984, 26, 45–51 and Ames et al., J. Chem. Soc. 1965, 2636–2641.

The starting 8-methoxy-2-tetralene was prepared as follows:

a. 8-Methoxy-2-tetralone

Following the procedure of J. W. Cornforth and Sir Robert Robinson, JCS 1855 (1949), a dry 250 ml 3-necked flask equipped with a magnetic stirring bar, a condenser and an addition funnel was charged with 5.6 gm (243 mmol) of sodium. From the addition funnel a solution of 1,7-dimethoxy naphthalene, 5.0 gm (26.5 mmol), in 30 ml of ethanol was added rapidly, resulting in vigorous reflux. Reflux was maintained with a heating mantle until all the sodium was consumed and the solution was then cooled. Water, 50 ml, was added followed by 55 ml of concentrated HCl and this solution was refluxed for 30 minutes. The cooled solution was extracted several times with ether, washed with water and the solvent was removed in vacuo. The residue was treated with 25 ml of saturated $NaHSO_3$ solution and stirred to form a solid which was collected by filtration and washed with ether. This solid in an erlenmeyer was treated with saturated $Na_2CO_3$ and ether and stirred until all the solid disappeared. The extract was washed with brine and dried ($Na_2SO_4$). Filtration and concentration in vacuo gave 2.83 gm (63%) of a pale yellow oil which solidified; homogeneous by tlc (silica gel; $CH_2Cl_2$), $R_f$ 0.25.

EXAMPLE 10

N-Methyl-2-amino-7-bromo-5,8-dimethoxy-tetralin Hydrochloride

As in Example 6, the crude formamide 10c (1.07 gm, 3.41 mmol) was reacted with 1.0M borane-THF (10.5 ml, 10.5 mmol) in THF at reflux for 8 hours to yield 0.913 gm of a pale yellow oil. Kugelrohr distillation (125° C., 0.05 mm Hg) yielded 0.838 gm (82%) of a colorless syrup; tlc (silica gel, 1:9 MeOH:$CH_2Cl_2$) $R_f$ 0.15. The entirety of crude amine was treated with ethereal HCl to yield a solid which was collected by filtration and dried under vacuum, to give 0.66 gm (71%), mp 190°–192° C.

The starting materials were prepared as follows:

a. 7-Bromo-3,4-dihydro-5,8-dimethoxy-2-nitronaphthalene

As in Example 6e, 2-bromo-1,4-dimethoxy-5,6-dihydronaphthalene* (2.13 g, 7.9 mmol) was reacted with iodine (4.22 g, 16.6 mmol), silver nitrite (2.54 g, 16.6 mmol), and pyridine (2.7 ml, 33 mmol) to yield a bright yellow solid (1.76 g, 72%), mp 128°–132° C.; tlc (silica gel, $CH_2Cl_2$) $R_f$ 0.65.

* prepared according to the procedure of M. Braun, Tetrahedron 40, 4585 (1984)

b. 2-Amino-7-bromo-5,8-dimethoxytetralin

As in example 6f, nitroolefin 10a, 1.70 gm, was reacted with sodium borohydride (1.23 g, 32.5 mmol) and boron trifluoride etherate (4.6 ml, 5.25 g, 37 mmol) in THF to give 1.53 gm of a pale yellow oil. Kugelrohr distillation (130° C., 0.04 mm Hg) gave 1.20 gm (75%) of a colorless syrup; tlc (silica gel, 1:9 MeOH:$CH_2Cl_2$) $R_f$ 0.15. A 0.20 g portion was treated with ethereal HCl, collected, and dried under vacuum to yield the hydrochloride (0.132 g, 59%); mp>270°.

c. N-Formyl-2-amino-7-bromo-5,8-dimethoxytetralin

As in Example 6g, amine 10b (1.00 g, 4.19 mmol) was added to a mixture of 98% formic acid (0.17 g, 4.6 mmol) and carbonyl diimidazole (0.75 g, 4.6 mmol) in THF to yield an off-white solid (1,07 g, 81%); tlc (silica gel, 1:9 MeOH:$CH_2Cl_2$) $R_f$ 0.65. This material was used without further purification.

EXAMPLE 11

N-Methyl-2-amino-6-bromo-5,8-dimethoxytetralin Hydrochloride

As in Example 6, N-formyl-2-amino-6-bromo-5,8-dimethoxytetralin, 458 mg (1.46 mmol), in 15 ml THF was reduced with 6 ml of 1.0M borane in THF by heating at reflux for 48 hr. The residue from the ether extraction was kugelrohr distilled to give 346 mg (52%) of a colorless oil, bp 125°–135° C. (air bath temperature) at 0.005 mm Hg. This oil in 5 ml ethanol was treated with 10 ml ethereal HCl to give a gummy precipitate. Dilution with 100 ml ether and trituration gave a white solid which was collected by filtration and dried in a drying pistol over refluxing methanol at 0.05 mm Hg to yield 246 mg, mp 173°–175° C.

The starting materials materials were prepared as follows:

a. 3-Bromo-2,5-dimethoxybenzyl Alcohol

A solution of 8.27 gm (33.75 mmol) of 3-bromo-2,5-dimethoxy benzaldehyde* in 40 ml THF and 20 ml water was cooled to 10° C. and treated portionwise with 3.83 gm (101.2 mmol) $NaBH_4$. Stirring was maintained at ambient temperature until tlc analysis (silica gel; 1:4 ethyl acetate:hexane) indicated the absence of starting aldehyde. After 30 minutes the solvent was removed in vacuo and the residue was portioned between ethyl acetate and water. After washing with brine and drying ($Na_2SO_4$), the ethyl acetate extract was concentrated in vacuo to yield 8.34 gm (99%) of a white solid, mp 59°–60° C.; tlc (cited), $R_f$ 0.12.

* prepared according to the procedure of J. S. Swenton and P. W. Raynolds, J. Am. Chem. Soc,. 100, 6188 (1978)

b. 3-Bromo-2,5-dimethoxybenzyl Chloride

To a solution of 8.18 gm (33.11 mmol) of 3-bromo-2,5-dimethoxybenzyl alcohol and 0.8 ml pyridine in 100 ml ether was added dropwise a solution of 8.5 ml (116 mmol) thionyl chloride in 20 ml ether. After stirring at ambient temperature for 20 hours, the reaction mixture was poured onto ice. The ether extract was washed with brine, dried ($NaSO_4$), filtered and concentrated in vacuo to give 7.59 gm of a colorless oil. A portion, 3.9 gm, was purified by silica gel chromatography using 3:7 $CH_2Cl_2$:hexane to yield 3.62 gm of a white solid.

c. 2-[3-(3-Bromo-2,5-dimethoxyphenyl)propyl]-1,3-dioxane

A solution of 2-(2-bromoethyl)-1,3-dioxane, 5.52 gm (28.32 mmol), in 25 ml dry THF was added to 0.72 gm (29.67 mmol) magnesium turnings and 10 mg iodine and heated to reflux for 2 hours. The cooled solution was added dropwise to a solution of 3.58 gm (13.49 mmol) of 3-bromo- 5,8-dimethoxybenzyl chloride in 25 ml THF at −10° C. This was followed by the addition of 0.70 ml (0.7 mmol) of 0.1M dilithium tetrachlorocuprate in THF. After 1.5 hours tlc analysis (silica gel; 1:4 ethyl acetate:hexane) indicated the absence of starting benzyl chloride ($R_f$ 0.65) and the presence of a major component at $R_f$ 0.54 and a minor component at $R_f$ 0.35 in addition to some base line material. The solvent was removed in vacuo and the residue was partitioned between ether and 5% ammonium chloride. The ether extract was washed with brine, dried over $Na_2SO_4$, filtered and the solvent was removed in vacuo. This material was kugelrohr distilled at 0.010 mm Hg (air bath temperature 120°–160° C.) to give a 2.93 gm of a colorless oil which was a mixture of the $R_f$ 0.35 component (now major) and the $R_f$ 0.54 component (now minor) and a pot residue, 0.75 gm, which was the $R_f$ 0.54 component. These components of the distilled material were separated by column chromatography using 140 gm of silica gel and eluting with 1:4 ethyl acetate:methylene chloride to give 1.15 gm (25%) of the titled dioxane as the later eluting material. The first eluting material of $R_f$ 0.54 proved to be the product of homo coupling of the benzyl chloride.

d. 6-Bromo-3,4-dihydro-5,8-dimethoxynaphthalene

A solution of 1.10 gm (3.19 mmol) of 2-[3-(3-bromo-2,5-dimethoxyphenyl)propyl]-1,3-dioxane and 300 mg p-toluene sulphonic acid in 10 ml absolute ethanol was refluxed for 48 hours at which time tlc analysis (silica gel, 1:4 ethyl acetate:hexane) indicated the absence of the dioxane. The solvent was removed in vacuo and the residue was partitioned between ether and 5% sodium carbonate. The ether extract was washed with brine, dried with $Na_2SO_4$, filtered and the solvent was removed in vacuo. The residue was kugelrohr distilled at 0.005 mm Hg to give 0.85 gm (99%) of a colorless oil, bp 95° C. (air bath temperature), homogeneous by tlc (ibid), $R_f$ 0.74.

e. 6-Bromo-3,4-dihydro-5,8-dimethoxy-2-nitronaphthalene

Silver nitrite, 1.00 gm (6.56 mmol), and iodine, 1.67 gm (6.56 mmol), in 15 ml THF were stirred for 30 minutes and cooled to 5° C. A solution of 0.84 gm (3.13 mmol) of 6-bromo-3,4-dihydro-5,8-dimethoxynaphthalene and 1.04 gm (4.2 mmol) pyridine in 15 ml THF was added dropwise and the reaction mixture was allowed to warm to ambient temperature over 30 minutes. The mixture was filtered through CELITE®, 1 ml triethylamine was added to the filtrate and the solvent was removed in vacuo. The residue was dissolved in 30 ml methylene chloride, treated with 2 ml triethylamine and stirred for 2.5 hours. The solvent was then removed in vacuo and the residue was partitioned between ethyl acetate and water. The ethyl acetate extract was washed twice with sodium bisulphite solution, water, 1N HCl, 5% sodium carbonate, brine and dried (sodium sulphate). Filtration and removal of solvent in vacuo left 0.90 gm of a brown solid. Column chromatograhy using 75 gm silica gel and eluting with methylene chloride gave the pure material, 0.64 gm (65%), mp 121°–123° C.; tlc (silica gel, $CH_2Cl_2$), $R_f$ 0.66.

f. 2-Amino-6-bromo-5,8-dimethoxytetralin

As in example 6f, 6-bromo-3,4-dihydro-5,8-dimethoxy-2-nitronaphthalene, 1.06 gm (3.37 mmol), in 25 ml THF was reduced with 0.66 gm (17.56 mmol) $NaBH_4$ in 25 ml THF and 2.5 ml (20.26 mmol) boron trifluoride etherate. The ether extract gave 1.05 gm which was kugelrohr distilled at 0.005 mm Hg to give 0.46 gm (45%) of a colorless oil, bp 125°–135° C. (air bath temperature), homogeneous by tlc (silica gel, 1:9 methanol:methylene chloride) $R_f$ 0.26.

g. N-Formyl-2-amino-6-bromo-5,8-dimethoxytetralin

Following a procedure similar to that described in example 6 g, but adding formic acid to carbonyl diimidazole rather than carbonyl diimidazole to formic acid, 2-amino-6-bromo-5,8-methoxytetralin, 458 mg (1.60 mmol) in 14 ml THF: methylene chloride (1:1) was formylated with 312 mg (1.92 mmol) carbonyl dimidazole in 10 ml THF and 88 mg (1.92 mmol) formic acid in 4 ml THF. After stirring for 20 hours. The residue obtained on removal of solvent was dissolved in ether, washed with 3N HCl, $Na_2CO_3$ solution, brine and dried ($MgSO_4$). Filtration and removal of solvent in vacuo left a white solid, 470 mg (94%), homogeneous by tlc (silica gel, 1:9 methanol: methylene chloride), $R_f$ 0.73.

EXAMPLE 12

(−)-N-Methyl-(2S)-2-amino-8-methoxytetralin

It is contemplated that (−)-N-methyl-(2S)-2-amino-8-methoxytetralin can be prepared as follows: (−)-(2S)-2-benzylamino-8-methoxytetralin (prepared as described in Karlsson et al., Acta Chemica Scandinavica 1988, B42, 231–236) can be hydrogenated in a Parr apparatus in the presence of 10% palladium on carbon to afford (−)-(2S)-2-amino-8-methoxy-tetralin. (−)-($^2$S)-2-Amino-8-methoxytetralin can then be formylated as described in Example 6(g) to afford (−)-N-formyl-(2S)-2-amino-8-methoxytetralin which in turn can be reduced as described in Example 6 to afford (−)-N-methyl-(2S)-2-amino-8-methoxytetralin.

EXAMPLE 13

(−)-N-Methyl-(2S)-2-amino-8-methoxytetralin Hydrochloride

As in Example 6, (−)-N-formyl-(2S)-2-amino-8-methoxytetralin (810 mg, 3.95 mmol) in 25 ml THF was added to 22 ml of borane (1.0M in THF) in 15 ml THF at 0° C. over 10 minutes and heated to reflux for 20 hr. After cooling, 10 ml water was added dropwise followed by 50 ml of 6N HCl and the solution was stirred overnight at ambient temperature. After basification with 50% sodium hydroxide to pH 14, an ethyl acetate extraction yielded 762 mg of a brown oil. Kugelrohr distillation gave 661 mg of a colorless oil, bp 95°–100° C. (air bath temperature) at 0.015 mm Hg. This oil, 655 mg, was dissolved in ether and treated with etheral HCl to give a white precipitate which was collected by filtration and dried in a drying pistol over refluxing methanol at 0.02 mm Hg to yield 632 mg, mp 201°–203° C. $[\alpha]_D^{22}$ −68° C. (c=0.75, methanol).

The starting material was obtained as follows:

a. (−)N-formyl-(2S)-2-amino-8-methoxytetralin

As in example 6g, (−)(2S)-2-amino-$^8$-methoxytetralin (commercially available) (825 mg, 4.66 mmol) in 10 ml THF and 20 ml methylene chloride, was formylated with 906 mg (5.59 mmol) carbonyl diimidazole in 15 ml THF and 257 mg (5.59 mmol) formic acid in 3 ml THF. After stirring overnight, TLC analysis (silica gel; 10:90 $CH_3OH:CH_2Cl_2$) indicated a major component, Rf 0.71, and absence of starting amine, Rf 0.22. The residue obtained on removal of solvent was dissolved in ethyl acetate, washed with 1N HCl, $NaHCO_3$ solution, brine and dried ($MgSO_4$). Filtration and removal of solvent in vacuo left a white solid, 850 mg (89%), mp 140°–141° C.

EXAMPLE 14

Following conventional procedures well known in the pharmaceutical art it is contemplated that the following representative pharmaceutical dosage forms containing a compound of formula I can be prepared.

| (a) Tablet | mg/tablet |
|---|---|
| Compound of Formula I | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |

| (b) Capsule | mg/capsule |
|---|---|
| Compound of Formula I | 10.0 |
| Mannitol, USP | 488.5 |
| Croscarmellose sodium | 15.0 |
| Magnesium stearate | 1.5 |

(c) Injection

A sterile aqueous solution for intravenous administration may be prepared by dissolving a compound of Formula I in distilled water containing hydroxypropylmethylcellulose (0.5% by weight) and Tween 80 (0.1% by weight). Thus, for example, an aqueous solution having the following composition may be prepared:

| Compound of Formula I | 3.5 g/l |
|---|---|
| Hydroxypropylmethylcellulose (HPMC), USP | 1.0 g/l |
| Tween 80 (polyoxyethylene sorbitan monooleate) | 5.0 g/l |

Certain disorders of the basal ganglia in the brain are known as extrapyramidal disorders which manifest as involuntary movements of two types. The first, hyperkinesia, causes an excess of movement. The second, hypokinesia, causes poverty of movement. Such movement disorders include, but are not limited to, myoclonus, Tourette's Syndrome, chorea, athetosis, choreoathetosis, Huntington's disease, and dystonias such as generalized dystonia, focal dystonias, Meinge Syndrome and Torticollis. Additionally, there are involuntary movement disorders caused by the use of neuroleptic drugs and antiparkinsonian drugs (e.g. levodopa). These involuntary movements include, but are not limited to, Parkinsonism, acute dystonia and tardive dsykinesia. It has been found that the dyskinetic reactions produced by antipsychotic (neuroleptic) drug administration (i.e. haloperidol) to sensitized cebus monkeys include a continuum of reactions, i.e. from very rapid contractions of a muscle group as in myoclonus to the slow writhing movements of dystonia. The similarities between the involuntary movement disorders seen in humans and the involuntary movements produced in sensitized cebus monkeys by neuroleptic drugs are:

1. The very rapid contraction of muscle groups seen after neuroleptic drug treatment are similar to those seen in myoclonus.

2. The licking movements seen after neuroleptic drug treatment may be on a continium with the vocal tics seen at the beginning of Tourette's Syndrome.

3. The brief involuntary movements of the face and limbs seen after neuroleptic drug treatment are very similar to the movements of chorea.

4. The slow writhing movements of the limbs and trunk seen after neuroleptic drug treatment are very similar to the movements seen in athetosis. Chorea and athetosis usually occur together and are referred to as choreoathetosis.

5. The slow writhing movements seen after neuroleptic drug treatment are also similar to the choreiform movements of Huntington's disease.

6. The sustained abnormal postures seen after neuroleptic drug treatment are similar to a variety of dystonias including:

a. generalized dystonia resulting in bizarre postures, b. focal dystonias of single body regions, c. Meinge syndrome involving jaw-grinding and grimacing, and d. Torticollis involving sustained torsion and deviation of the head and neck.

7. The involuntary movements seen after neuroleptic drug treatment are very similar to the involuntary movements found in Parkinsonism, acute dystonia and tardive dyskinesia.

Based on the similarities between the involuntary movement disorders seen in humans and the involuntary movements produced in sensitized cebus monkeys by neuroleptic drugs, it is believed that the ability of a compound to suppress the involuntary movements produced in sensitized cebus monkeys correlates with its usefulness in the treatment or prevention of movement disorders in mammals and in particular in man.

Representative examples of the compounds of the instant invention have been found to possess valuable pharmacological properties. In particular, they have been found to suppress the involuntary movements produced by neuroleptic drugs in sensitized cebus monkeys and are thus useful in the treatment or prevention of movement disorders, such as myoclonus, Tourette's Syndrome, chorea, athetosis, choreoathetosis, Huntington's disease, Parkinsonism, tardive dyskinesia and dystonias (including generalized dystonias, focal dystonias, acute dystonias, Meinge Syndrome and Torticollis), especially tardive dyskinesia.

Treatment using a compound of the invention can be remedial or therapeutic as by administering a compound of the invention to a patient who has already developed a movement disorder. Treatment can also be prophylactic or prospective as by administering a compound of the invention to a patient in anticipation that a movement disorder will occur, for example in a patient who is taking a neuroleptic drug or antiparkinsonian drug, in order to prevent such movement disorder from occurring. The compound of the invention can be administered as a separate medication, or as a combination medication with a neuroleptic or antiparkinsonian drug.

The pharmaceutical properties of representative examples of the compounds of the invention were demonstrated by the following conventional biological test procedures.

Initially, the racemic compounds of the instant invention are tested for dopamine antagonist activity as described hereinbelow and if the compounds are found to be active (see Table 1)they are tested in sensitized cebus monkeys according to the "dyskinesias in haloperidol-sensitized cebus monkeys" test described below (see Table 2). If, however, the racemic compounds are found not to be active as dopamine antagonists (see Table 1), then they or the corresponding S(-) enantiomer thereof, are tested directly in the "suppression of haloperidol-induced dyskinesias in haloperidol-sensitized cebus monkeys" test described below in Table 3.

Tests For Dopamine Antagonism

1. Antagonism of Apomorphine-induced Climbing

Female Swiss-Webster mice weighing approximately 20 grams were deprived of food for approximately 24 hours and then dosed intra-peritoneally(ip), orally(po) or subcutaneously (sc) with various doses of vehicle or a compound to be tested over a range of doses (N=20 mice per treatment group). Thirty minutes later they were administered apomorphine HCl at 1.25 mg/kg sc and placed into climbing cages. These cages were 9 cm wide, 15 cm deep and 30 cm high. One wall had 27 horizontal rungs spaced 1 cm apart. Thirteen minutes after apomorphine each mouse was observed continuously for one minute and the highest and lowest rung reached by its front paws was recorded. The mean of these two scores was used as the score for that mouse. The highest and lowest potential scores were 27 and 0, respectively.

2. Normalization of Apomorphine-induced Disruption of Swimming in Mice

Immediately after the 1 minute climbing observation period in the above test, each mouse was placed into a circular swimming tank for 2 minutes and the number of "swims" were counted. The height of the tank was 15 cm and the diameter was 28 cm. A circular obstacle, 10.5 cm in diameter and 17 cm high, was placed in the center of the tank, creating a circular swimming channel 8.75 cm wide. The water level was 5.5 cm and the water was kept at room temperature. Marks were placed on the floor and side of the tank 180 degrees apart. A "swim" was scored each time a mouse swam from one mark to the other and the median number of swims for all the mice was used as the score for that treatment. The mice were observed through overhead mirrors, and the number of 180 degree swims was recorded for each mouse. The mice were observed at all times for side effects of the drugs being tested, such as salivation, tremor, stimulation, piloerection, etc.

Table 1 summarizes the results obtained from testing representative compounds of the invention, as well as an example of a corresponding (R)(+) enantiomer thereof (Example 3), in the "Normalization of apomorphine-induced disruption of swimming in mice test". We report here only the results of the apomorphine-induced disruption of swimming in mice test since compounds which were active in this test were also found to be active in the antagonism of apomorphine-induced climbing test.

TABLE 1

| Example No. | Swimming Test (dose mg/kg ip) | Median Number of swims |
| --- | --- | --- |
| 1 | 2.5 | 0 |
|   | 5 | 0 |
|   | 10 | 20 |
|   | 20 | 27 |
|   | 40 | 29 |
| 2 | Inactive |   |
| 3 | 2.5 | 7 |
|   | 5 | 27 |
|   | 10 | 38 |
|   | 20 | 42 |
|   | 40 | 38 |
| 5 | Inactive |   |
| 6 | 2.5 | 0 |
|   | 5 | 0 |
|   | 10 | 0 |
|   | 20 | 15 |
|   | 40 | 41 |
| 7 | 2.5 | 0 |
|   | 5 | 0 |
|   | 10 | 0 |
|   | 20 | 4 |
|   | 40 | 16 |
| 8 | 2.5 | 0 |
|   | 5 | 0 |
|   | 10 | 0 |
|   | 20 | 16 |

TABLE 1-continued

| Example No. | Swimming Test (dose mg/kg ip) | Median Number of swims |
| --- | --- | --- |
| 9 | Inactive |   |
| 10 | 2.5 | 8 |
|   | 5 | 24 |
|   | 10 | 22 |
|   | 20 | 38 |
| 11 | Inactive |   |

Dyskinesias in Haloperiodol-sensitized Cebus Monkeys

Adult female or male cebus monkeys served as subjects. They were dosed with 1 mg/kg of haloperidol orally, once per week, until dyskinetic reactions occurred. These dyskinetic reactions consisted of any one or more of the following busso-oral movements: repetitive tongue protrusions, repetitive biting or licking of the bars of the cage; and the following choreoathetoid-like movements: various twisting and/or jerking movements of the arms or legs, twisting of the torso or neck. When these dyskinetic reactions occurred reliably over a period of weeks the monkeys were considered to be "sensitized", and could be used to test for the occurrence of dyskinetic reactions to other drugs such as the compounds of the instant invention. The interval between drug treatments was at least 2 weeks. Representative compounds of the instant invention were administered orally at the doses indicated in Table 2. After dosing, the monkey was immediately returned to its home cage. Two observers working in 1–3 hour shifts then observed each monkey continuously for dyskinetic reactions for 6–7 hours after drug administration. Every 30 minutes the observer recorded the type of reaction that had occurred and its severity. For repetitive reactions such as tongue protrusions, the observer recorded the number of such movements in 1-minute samples.

Table 2 summarizes the results obtained from the testing of representative compounds of the instant invention for dyskinesias in haloperidol-sensitized cebus monkeys.

TABLE 2

| Example No. | Dose (mg/kg po) | # dyskinetic/# tested |
| --- | --- | --- |
| 1 | 5 | 0/6 |
|   | 10 | 0/13 |
|   | 20 | 0/3 |
| 3 (R(+)-enantiomer) | 5 | 3/4 |
| 6 | 5 | 0/6 |
|   | 10 | 0/6 |
|   | 20 | 0/7 |
| 7 | 20 | 0/3 |
| 8 | 5 | 1/2 (weak) |
|   | 10 | 0/2 |
|   | 20 | 0/2 |

Suppression of Haloperidol-induced Dyskinesias in Haloperidol-sensitized Cebus Monkeys To test for the ability of a representative compound of the instant invention to suppress neuroleptic-induced dyskinesias the compound was administered at the doses indicated in Table 3 simultaneously with a standard dose, 0.25 mg/kg p.o., of haloperidol. This dose of haloperidol typically produced dyskinetic reactions within one or two hours in all monkeys, with the reactions usually lasting several hours. Sensitized cebus monkeys as described above served as subjects. After the coadministration of haloperidol and the compound being tested, the test proceeded as described above for "Dyskinesias in haloperidol-sensitized cebus monkeys".

Table 3 summarizes the results obtained from the testing of representative compounds of the instant invention in the suppression of haloperidol-induced dyskinesias in haloperidol-sensitized cebus monkeys test.

TABLE 3

| Example No. | Dose (mg/kg po) | # dyskinetic/# tested |
|---|---|---|
| 2 | 10 | 0/5 |
| 5 | 10 | 1/4 |
| 9 | 20 | 0/4 |

The results from Tables 1–3 illustrate that for the treatment of movement disorders, the active component of the compounds of the instant invention is the S(−) form (i.e. Example 2) and that the R(+)-form (i.e. Example 3) is responsible for any of the exhibited dopamine antagonism activity and for the production of dyskinesias. It will also be appreciated that for the compounds of the instant invention that are in the (R,S) form, the S(−)-enantiomer contained therein is an effective enough of a suppressor of movement disorders in order to suppress the dyskinetic activity of the corresponding R(+)-enantiomer.

The ability of the compound of Example 2, a representative example of the compounds of the instant invention, to suppress movement disorders, i.e. dykinesias, caused by the administration of dyskinetic aminotetralin derivatives (i.e. Example 10 described herein) or various antipsychotic (neuroleptic) drugs, such as chlorpromazine, thioridazine, haloperidol and the like, was demonstrated by utilizing the "Suppression of haloperidol-induced dyskinesias in haloperidol-sensitized cebus monkeys test procedure described hereinabove, but substituting, where appropriate, an appropriate dose (in mg/kg po) of a dyskinetic aminotetralin derivative or neuroleptic drug for 0.25 mg/kg po of haloperidol. Table 4 summarizes the results obtained from the testing of the compound of Example 2 in this test procedure.

TABLE 4

| Test Agent | Dose (Mg/kg po) Test Agent | Dose (Mg/kg po) Compound of Example 2 | # dyskinetic/# tested |
|---|---|---|---|
| Compound of Example 10 | 5 | 0 | 4/6 |
|  | 5 | 10 | 0/6 |
| Chlorpromazine | 5 | 0 | 3/3 |
|  | 5 | 10 | 0/3 |
| Thioridazine | 10 | 0 | 5/5 |
|  | 10 | 10 | 0/5 |
| Haloperidol | 0.25 | 0 | 5/5 |
|  | 0.25 | 10 | 0/5 |

The compounds of the invention are generally administered to patients which include, but are not limited to, mammals such as, for example, man. It will also be apparent to those skilled in the art that a compound according to the invention can be coadministered with other therapeutic or prophylactic agents and/or medicaments that are not medically incompatible therewith. In general, representative compounds of the instant invention do not show any indication of overt toxicity in laboratory test animals.

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more pharmaceutically acceptable carriers, adjuvants, diluents or vehicles, for oral administration in solid or liquid form, parenteral administration, topical administration, rectal administration, or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such was water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

Preparations according to the invention for rectal administration include suppositories prepared by using suitable carriers, e.g., cacao butter, hardened oils, glycerides or saturated fatty acids and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinicians judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf. In general, a compound of the instant invention is administered at a dose in the range of about 0.01 to about 100 mg/kg body weight.

What is claimed is:

1. A compound of the formula I:

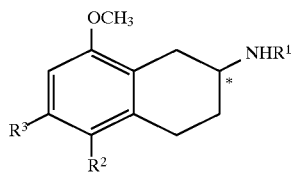

wherein:
R¹ is methyl; R² is hydrogen, halogen, lower-alkoxy or thiolower-alkyl; R³ is hydrogen, halogen, lower-alkoxy or lower-alkyl; and the chiral center * is in the (S)(−) form; or a pharmaceutically acceptable acid-addition salt thereof.

2. A compound according to claim 1 wherein R² is hydrogen, bromo, methoxy, ethoxy or thiomethyl; and R³ is hydrogen or halogen.

3. A compound according to claim 2 wherein R³ is hydrogen.

4. A compound according to claim 3 selected from the group consisting of (−)-N-Methyl-(2S)-2-amino-5,8-dimethoxytetralin hydrochloride and (−)-N-methyl-(2S)-2-amino-8-methoxytetralin.

5. (−)-N-Methyl-(2S)-2-amino-8-methoxytetralin hydrochloride according to claim 3.

6. A pharmaceutical composition for the treatment or prevention of movement disorders in a patient in need of such treatment which comprises a compound according to any one of claims 1–5 together with a pharmaceutically acceptable carrier, adjuvent, diluent, or vehicle.

7. A method for the treatment or prevention of movement disorders which comprises administering to a patient in need of such treatment an effective amount of a compound of the formula I:

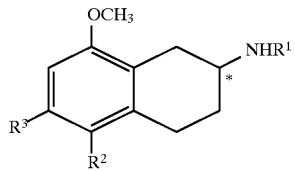

wherein:
R¹ is methyl or ethyl; R² is hydrogen, halogen, lower-alkoxy, or thiolower-alkyl; R³ is hydrogen, halogen, lower-alkoxy or lower-alkyl; and the chiral center * is in the (S) (−) form or the (R,S) form; or a pharmaceutically acceptable acid-addition salt thereof; with the provisos that (a) when R² and R³ are both hydrogen, R¹ must be methyl and (b) when the chiral center * is in the (R,S) form the proportion of the (S)(−) form must be 50% or greater.

8. A method according to claim 7 wherein the chiral center * is in the (S)(−) form.

9. A method according to claim 8 wherein R² is hydrogen, bromo, methoxy, ethoxy, or thiomethyl, and R³ is hydrogen or halogen.

10. A method according to claim 9 wherein R³ is hydrogen.

11. A method according to claim 10 wherein the compound is selected from the group consisting of (−)-N-methyl-(2S)-2-amino-5,8-dimethoxytetralin hydrochloride and (−)-N-methyl-(2S)-2-amino-8-methoxytetralin.

12. A method according to claim 10 wherein the compound is (−)-N-methyl-(2S)-2-amino-8-methoxytetralin hydrochloride.

13. A method according to claim 7 wherein the compound is selected from the group consisting of:
N-methyl-2-amino-5,8-dimethoxytetralin hydrochloride;
(−)-N-methyl-(2S)-2-amino-5,8-dimethoxytetralin hydrochloride;
N-ethyl-2-amino-5,8-dimethoxytetralin hydrochloride;
(−)-N-ethyl-(2S)-2-amino-5,8-dimethoxytetralin hydrochloride;
N-methyl-2-amino-5-bromo-8-methoxytetralin hydrochloride;
N-methyl-2-amino-8-methoxy-5-thiomethyltetralin hydrochloride;
N-methyl-2-amino-5-ethoxy-8-methoxytetralin hydrochloride;
N-methyl-2-amino-6-bromo-5,8-dimethoxytetralin hydrochloride;
(−)-N-methyl-(2S)-2-amino-8-methoxytetralin; and
N-methyl-2-amino-8-methoxytetralin hydrochloride.

14. A method according to claim 7 wherein the movement disorder is tardive dyskinesia.

15. A method according to claim 7, wherein the movement disorder is Parkinson's Disease.

16. A process for preparing a compound of the formula I:

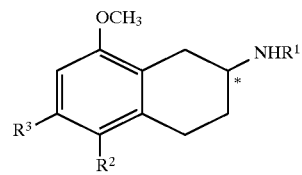

wherein:
R¹ is methyl or ethyl; R² is hydrogen, halogen, lower-alkoxy or thiolower-alkyl; R³ is hydrogen, halogen, lower-alkoxy or lower-alkyl; and the chiral center * is in the (S)(−) form; or a pharmaceutically acceptable acid-addition salt thereof, with the proviso that when R² and R³ are both hydrogen, R¹ must be methyl;
which comprises reacting a single enantiomer of a compound of the formula VIII:

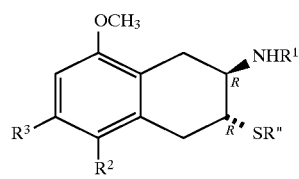

wherein R" is lower-alkyl, with a reducing agent.

* * * * *